US012749902B2

(12) United States Patent
Li et al.

(10) Patent No.: US 12,749,902 B2
(45) Date of Patent: Sep. 29, 2026

(54) POWER MANAGEMENT METHOD, SYSTEM, DEVICE AND MEDIUM FOR LIFE SUPPORT EQUIPMENT

(71) Applicant: Lifemotion Medical Technology Co., Ltd., Shenzhen (CN)

(72) Inventors: Yijiang Li, Shenzhen (CN); Yu Wu, Shenzhen (CN); Yang Liu, Shenzhen (CN); Mingtao Li, Shenzhen (CN)

(73) Assignee: Lifemotion Medical Technology Co., Ltd., Shenzhen (CN)

( * ) Notice: Subject to any disclaimer, the term of this patent is extended or adjusted under 35 U.S.C. 154(b) by 0 days.

(21) Appl. No.: 18/988,743

(22) Filed: Dec. 19, 2024

(65) Prior Publication Data

US 2025/0219438 A1 Jul. 3, 2025

(30) Foreign Application Priority Data

Dec. 28, 2023 (CN) ......................... 202311838904.7

(51) Int. Cl.
*H02J 1/10* (2026.01)
*A61M 1/14* (2006.01)
(Continued)

(52) U.S. Cl.
CPC ................. *H02J 7/34* (2013.01); *A61M 1/14* (2013.01); *H02J 7/50* (2026.01); *H02J 7/80* (2026.01);
(Continued)

(58) Field of Classification Search
CPC .......... H02J 7/34; H02J 7/0013; H02J 7/0047; H02J 7/0063; H02J 7/00712; H02J 1/108;
(Continued)

(56) References Cited

U.S. PATENT DOCUMENTS

2009/0160500 A1 6/2009 Niculae et al.

FOREIGN PATENT DOCUMENTS

JP WO2016063866 * 4/2016
JP 2021072663 * 5/2021
(Continued)

OTHER PUBLICATIONS

Extended European Search Report issued in EP 24222991.2, dated Jul. 7, 2025.

*Primary Examiner* — Rexford N Barnie
*Assistant Examiner* — Xuan Ly
(74) *Attorney, Agent, or Firm* — Nelson Mullins Riley & Scarborough LLP

(57) ABSTRACT

A power management method, system, device and medium for life support equipment, when it is detected that the power of the external energy storage power supply is insufficient to power the whole device, the charging power of the battery is reduced by adjusting the duty cycle. At the same time, a prediction algorithm is added when adjusting the duty cycle to reduce the probability of the external energy storage power supply triggering overload protection. In this way, when the power of the external energy storage power supply is insufficient, it can ensure that the internal battery has more power, thereby improving the endurance of the ECMO device when transferring patients and better ensuring the life safety of patients.

12 Claims, 9 Drawing Sheets

(51) Int. Cl.

| | |
|---|---|
| ***A61M 1/36*** | (2006.01) |
| ***H02J 7/00*** | (2026.01) |
| ***H02J 7/34*** | (2006.01) |
| ***H02J 7/50*** | (2026.01) |
| ***H02J 7/80*** | (2026.01) |
| ***H02J 7/90*** | (2026.01) |
| ***H02J 9/00*** | (2006.01) |

(52) U.S. Cl.
CPC .............. *H02J 7/855* (2026.01); *H02J 7/933* (2026.01); *A61M 2205/8212* (2013.01)

(58) Field of Classification Search
CPC ........ H02J 7/0024; H02J 7/0025; H02J 9/005; H02J 2310/23; H02J 7/0068; H02J 7/0071; H02J 1/10; H02J 7/00; H02J 9/00; A61M 1/14; A61M 2205/8212; A61M 2205/8206; A61M 2205/8237; A61M 1/3666; A61M 1/36
USPC ........................................................ 307/20
See application file for complete search history.

(56) References Cited

FOREIGN PATENT DOCUMENTS

| | | | |
|---|---|---|---|
| JP | 2021072663 | A | 5/2021 |
| WO | 2016063866 | A1 | 4/2016 |
| WO | 2018028316 | A1 | 2/2018 |

* cited by examiner

Instruction Manual

POWER MANAGEMENT METHOD, SYSTEM, DEVICE AND MEDIUM FOR LIFE SUPPORT EQUIPMENT

CROSS REFERENCE TO RELATED APPLICATION

The present application claims priority to Chinese Patent Application No. 202311838904.7, filed Dec. 28, 2023, the entire disclosure of which is incorporated herein by reference.

TECHNICAL FIELD

The embodiments of the present invention relate to the technical field of life support medical equipment, and in particular to a power management method, system, equipment and medium for life support equipment.

BACKGROUND

Extracorporeal membrane oxygenation (ECMO) is an emergency or life support device often used in ambulances, helicopters or other outdoor scenes.

ECMO equipment is used in outdoor scenarios, where 220 V AC power is usually not available. It is generally powered by a vehicle power supply or other energy storage batteries. However, the external energy storage power supply may not have enough power. When the power required by the device is greater than the power that the external energy storage power supply can provide, the external energy storage power supply will cut off the power supply due to overload protection. Although the patent with publication number CN113541263A provides a method for automatically switching circuits between external power supply and battery power supply for a portable device, the device can only be powered by the mutual exchange of external power supply and battery, and the device needs to be turned on and off to achieve this, which obviously cannot provide help for the endurance of ECMO equipment. In addition, the patent with publication number CN116581846A provides a method and system for intelligently controlling battery charging, but when the power of the external energy storage power supply is lower than the power required by the device, the main frequency and power consumption of the electronic device need to be reduced, so it is not suitable for ECMO equipment.

ECMO equipment is a life-support device. Reducing the power consumption of the equipment will affect its performance and cause unpredictable effects on patients. If the power consumption of the equipment is not reduced or the minimum protection unit cannot continue to reduce the power consumption after the power consumption of part of the equipment has been reduced, the external energy storage power supply will be powered off due to overload protection, which is not conducive to the endurance of the equipment. Therefore, a power management solution is needed to improve the power supply endurance of medical equipment such as ECMO equipment.

SUMMARY

To this end, embodiments of the present invention provide a power management method, system, device and medium for life support equipment to solve the technical problem that when an external energy storage power supply is insufficient in power, the power is prematurely cut off due to overload triggering protection, resulting in a short power supply endurance time of the medical equipment.

In order to achieve the above objectives, the embodiments of the present invention provide the following technical solutions:

According to a first aspect of an embodiment of the present invention, an embodiment of the present invention provides a power management method for a life support device, the method comprising:

The method is applied to a power management module, comprising:

- Performing a first real-time monitoring of the voltage of the external energy storage power supply;
- If the voltage of the external energy storage power supply does not meet the first preset condition, the external power supply is controlled to directly power the main device, the first battery and the second battery are charged at the same time, and the voltage of the external energy storage power supply is continuously monitored in a first real-time manner;
- If the voltage of the external energy storage power supply meets the first preset condition, the first charging power duty cycle of the first battery and the second battery is reduced according to a first preset ratio;
- Record the number of first-stage adjustments and the corresponding first-stage adjustment time;
- Using the first preset number of recorded first-stage adjustment times and the corresponding first-stage adjustment times, predict the next first-stage voltage adjustment time;
- Before the predicted next first-stage adjustment time, the first preset time threshold is advanced, and the first charging power duty cycle of the first battery and the second battery continues to be reduced according to the first preset ratio;
- Among them, the first preset condition is set as the voltage of the external energy storage power supply being lower than a first preset threshold value for a continuous first time period, the first time period is 500 milliseconds-1000 milliseconds, and the first preset threshold value is 90%-95% of the normal value of the external energy storage power supply voltage.

Further, using the recorded first preset number of first-stage adjustment times and the corresponding first-stage adjustment times, predicting the next first-stage adjustment time includes:

- Determine whether the current first-stage adjustment times reaches the first preset number;
- If the current first-stage adjustment times do not reach the first preset number, continue to perform the first real-time monitoring of the external energy storage power supply voltage;
- If the current first-stage adjustment times reaches the first preset number, the first-stage adjustment time difference between two adjacent first-stage adjustment times is calculated in sequence;
- Determine whether the time differences of each first-stage adjustment satisfy the requirement of increasing or decreasing in sequence;
- straight line adjustment function between the time differences of the first-stage adjustment and the corresponding number of first-stage adjustment times is fitted;
- If the time differences of the first-stage adjustment do not satisfy the requirement of increasing or decreasing in sequence, then calculating a first average value of the time differences of the first-stage adjustment;

The first-stage adjustment function/the first average value is used to predict the next first-stage adjustment time.

Furthermore, the method further comprises:

Performing a second real-time monitoring on the first charging power duty cycle of the first battery and the second battery;

If the first charging power duty ratio of the first battery and the second battery does not meet the second preset condition, continue to perform second real-time monitoring on the first charging power duty ratio of the first battery and the second battery; the second preset condition is set as the first charging power duty ratio of the first battery and the second battery is reduced to 0;

If the first charging power duty ratios of the first battery and the second battery meet the second preset condition, performing a third real-time monitoring on the power levels of the first battery and the second battery;

If the power levels of the first battery and the second battery meet a third preset condition, controlling the external power supply and the first battery and the second battery to be connected in parallel to supply power to the main device;

If the power levels of the first battery and the second battery do not meet the third preset condition, the battery with higher power level is selected and marked as the power supply battery, and the other battery is marked as the rechargeable battery;

Switching the power supply battery to power the main device, and controlling the external power supply to only charge the rechargeable battery;

Among them, the third preset condition is set as the first power value of the first battery and the second power value of the second battery both do not reach their respective corresponding second preset thresholds, and the second preset thresholds corresponding to the first battery and the second battery are respectively 1%-5% of their own power.

Furthermore, the method further comprises:

If the power levels of the first battery and the second battery do not meet the third preset condition, performing a fourth real-time monitoring on the power levels of the first battery and the second battery;

If the power levels of the first battery and the second battery meet a fourth preset condition, performing a fifth real-time monitoring on the power levels of the current power supply battery and the current charging battery;

If the power levels of the current power supply battery and the current charging battery do not meet the fifth preset condition, continue to perform fourth real-time monitoring on the power levels of the first battery and the second battery;

If the power levels of the current power supply battery and the current rechargeable battery meet the fifth preset condition, then reselect the battery with higher power level as the power supply battery and mark the other battery as the rechargeable battery;

Switching the updated power supply battery to power the main device, controlling the external power supply to charge only the updated rechargeable battery, and continuing to perform a fourth real-time monitoring of the power of the first battery and the second battery;

Among them, the fourth preset condition is set as one of the first power value of the first battery and the second power value of the second battery exceeds their respective corresponding third preset thresholds, and the third preset thresholds corresponding to the first battery and the second battery are 3%-8% respectively; the fifth preset condition is set as the power value of the current power supply battery is less than the first preset ratio of the power value of the current charging battery, and the first preset ratio is 92%-97%.

Furthermore, the method further comprises:

If the power levels of the first battery and the second battery do not meet the fourth preset condition, performing a sixth real-time monitoring on the power levels of the current power supply battery and the current charging battery;

If the power levels of the current power supply battery and the current charging battery do not meet the sixth preset condition, continue to perform fourth real-time monitoring on the power levels of the first battery and the second battery;

If the power levels of the current power supply battery and the current rechargeable battery meet the sixth preset condition, then reselect the battery with higher power level as the power supply battery and mark the other battery as the rechargeable battery;

Switching the updated power supply battery to power the main device, controlling the external power supply to charge only the updated rechargeable battery, and continuing to perform a fourth real-time monitoring of the power of the first battery and the second battery;

The sixth preset condition is set as a second preset ratio that the power value of the current power supply battery is less than the power value of the current charging battery, and the second preset ratio is 99%-99.7%.

Furthermore, the method further comprises:

If the power levels of the first battery and the second battery do not meet the fourth preset condition, performing a seventh real-time monitoring on the voltage of the external energy storage power supply;

If the voltage of the external energy storage power supply does not meet the seventh preset condition, the seventh real-time monitoring of the voltage of the external energy storage power supply continues; the seventh preset condition is set as the voltage of the external energy storage power supply being lower than the fourth preset threshold value for a second consecutive time period, the second time period being 100 milliseconds to 200 milliseconds, and the fourth preset threshold being 96% to 98% of the normal value of the voltage of the external energy storage power supply;

If the voltage of the external energy storage power supply meets the seventh preset condition, the second charging power duty cycle of the rechargeable battery is reduced according to a second preset ratio;

Record the number of second-stage adjustments and the corresponding second-stage adjustment time;

Using the recorded second preset number of second-stage adjustment times and the corresponding second-stage adjustment times, predicting the next second-stage adjustment time;

Before the predicted next second-stage adjustment time, the second preset time threshold is advanced, and the second charging power duty cycle of the rechargeable battery is continued to be reduced according to the second preset ratio;

Performing an eighth real-time monitoring on the second charging power duty cycle of the rechargeable battery;

If the second charging power duty cycle of the rechargeable battery does not meet the eighth preset condition, continue to perform the eighth real-time monitoring on the second charging power duty cycle of the rechargeable battery; the eighth preset condition is set as the second charging power duty cycle of the rechargeable battery being reduced to 0;

If the second charging power duty cycle of the rechargeable battery meets the eighth preset condition, the external power supply and the first battery and the second battery are controlled to be connected in parallel to supply power to the main device.

Further, using the recorded second preset number of second-stage adjustment times and the corresponding second-stage adjustment times, predicting the next second-stage adjustment time includes:

Determining whether the current second-stage adjustment times reaches the second preset number;

If the current second-stage adjustment times do not reach the second preset number, continue to perform a seventh real-time monitoring of the external energy storage power supply voltage;

If the current second-stage adjustment times reaches the second preset number, the second-stage adjustment time difference between two adjacent second-stage adjustment times is calculated in sequence;

Determine whether the time differences of each second-stage adjustment satisfy the requirement of increasing or decreasing in sequence;

linear adjustment function between each second-stage adjustment time difference and the corresponding second-stage adjustment times is fitted;

If the time differences of the second-stage adjustment do not satisfy the requirement of increasing or decreasing in sequence, then calculating a second average value of the time differences of the second-stage adjustment;

The next second-stage adjustment time is predicted using the second-stage adjustment function/the second average value.

According to a second aspect of an embodiment of the present invention, an embodiment of the present invention provides a power management system for a life support device, the system is applied to a power management module, the system comprises: an external energy storage power supply voltage monitoring unit, a battery monitoring unit and a circuit control unit, The external energy storage power supply voltage monitoring unit performs a first real-time monitoring on the external energy storage power supply voltage;

If the voltage of the external energy storage power supply does not meet the first preset condition, the circuit control unit controls the external power supply to directly power the main device, and charges the first battery and the second battery at the same time, and the external energy storage power supply voltage monitoring unit continues to perform first real-time monitoring on the voltage of the external energy storage power supply;

If the voltage of the external energy storage power supply meets the first preset condition, the circuit control unit reduces the first charging power duty cycle of the first battery and the second battery according to a first preset ratio;

The circuit control unit records the number of first-stage adjustment times and the corresponding first-stage adjustment time; predicts the next first-stage adjustment time by using the recorded first preset number of first-stage adjustment times and the corresponding first-stage adjustment time; and continues to reduce the first charging power duty ratio of the first battery and the second battery according to the first preset ratio by a first preset time threshold before the predicted next first-stage adjustment time;

Among them, the first preset condition is set as the voltage of the external energy storage power supply being lower than a first preset threshold value for a continuous first time period, the first time period is 500 milliseconds-1000 milliseconds, and the first preset threshold value is 90%-95% of the normal value of the external energy storage power supply voltage.

According to a third aspect of an embodiment of the present invention, there is provided a power management system for a life support device, the device comprising: a processor and a memory;

The memory is used to store one or more program instructions;

The processor is used to run one or more program instructions to execute the steps of a power management method for a life support device as described in any one of the above items.

According to a fourth aspect of an embodiment of the present invention, a computer-readable storage medium is provided, on which a computer program is stored. When the computer program is executed by a processor, the steps of a power management method for a life support device as described in any one of the above items are implemented.

the power management method, system, device and medium of a life support device provided in the embodiment of the present application, for life support devices, when it is detected that the power of the external energy storage power supply is insufficient to power the whole device, the charging power of the battery is reduced by adjusting the duty cycle. At the same time, a prediction algorithm is added when adjusting the duty cycle to reduce the probability of the external energy storage power supply triggering overload protection. In this way, when the power of the external energy storage power supply is insufficient, the internal battery can be guaranteed to have more power, thereby improving the battery life of the ECMO device when transferring patients and better protecting the patient's life safety.

BRIEF DESCRIPTION OF THE DRAWINGS

The following briefly introduces the drawings required for the implementation methods or the description of the prior art. Obviously, the drawings in the following description are only exemplary, and for ordinary technicians in this field, other implementation drawings can be derived from the provided drawings without creative work.

The structures, proportions, sizes, etc. illustrated in this specification are only used to match the contents disclosed in the specification so as to facilitate understanding and reading by persons familiar with the technology. They are not used to limit the conditions under which the present invention can be implemented, and therefore have no substantial technical significance. Any structural modification, change in proportion or adjustment of size shall still fall within the scope of the technical contents disclosed in the present invention without affecting the effects and purposes that can be achieved by the present invention.

DETAILED DESCRIPTION

The following is a description of the implementation of the present invention by specific embodiments. People familiar with the art can easily understand other advantages and effects of the present invention from the contents disclosed in this specification. Obviously, the described embodiments are part of the embodiments of the present invention, not all of the embodiments. Based on the embodiments of the present invention, all other embodiments obtained by ordinary technicians in this field without creative work are within the scope of protection of the present invention.

The purpose of this application is to monitor and manage power supplies for high-life support medical equipment to prevent premature power outages due to overload protection when the external energy storage power supply is insufficient, thereby extending the power supply life of the medical equipment as much as possible.

Figure 1:
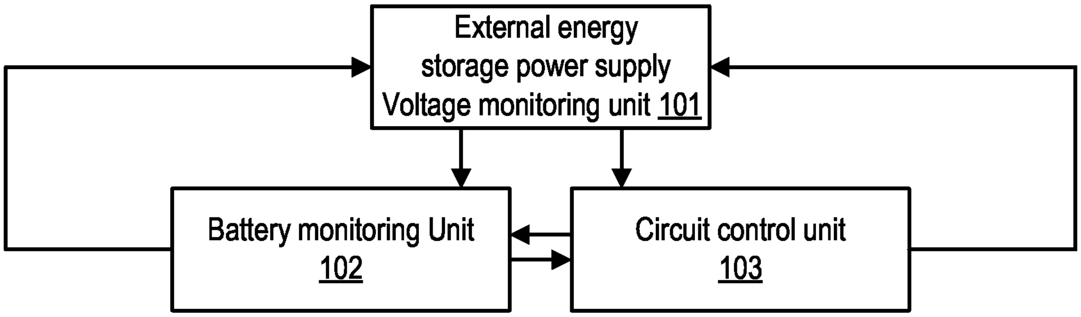
FIG. 1 is a schematic diagram of the logical structure of a power management system for a life support device provided by an embodiment of the present invention.
Figure 2:
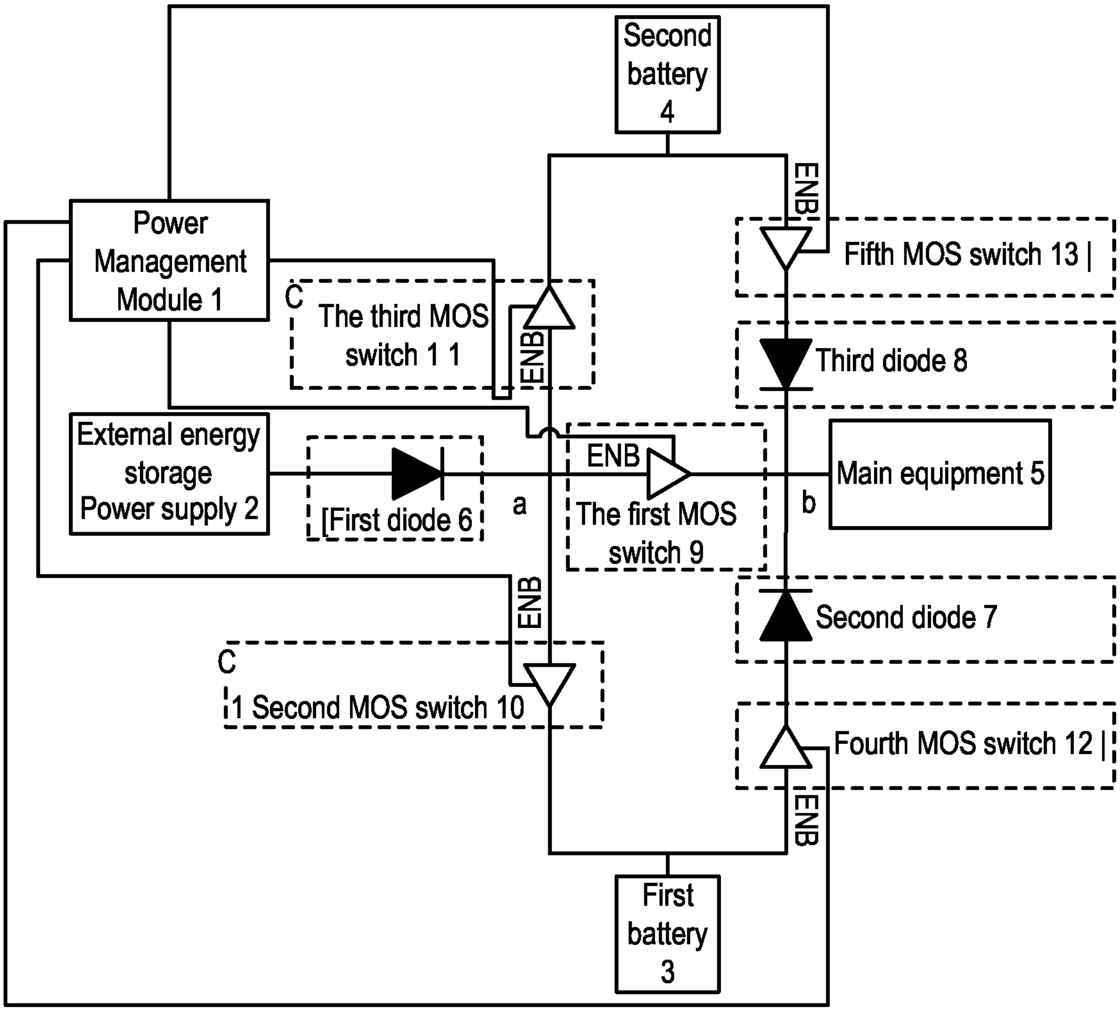
FIG. 2 is a schematic diagram of a power management circuit for implementing the corresponding functions of a power management module provided by an embodiment of the present invention.

In order to solve the above technical problems, as shown in FIG. 1, an embodiment provides a power management system for a life support device, which is applied to a power management module 1 (shown in FIG. 2).

In embodiments, the power management module 1 includes an MCU (Microcontroller Unit), whose main functions are to monitor the voltage of the external energy storage power supply, monitor the battery power and control the switch circuit.

Specifically, an embodiment of the present application provides a power management system for a life support device, including: an external energy storage power supply voltage monitoring unit 101, a battery monitoring unit 102 and a circuit control unit 103.

With reference to FIG. 2, a power management circuit for realizing the above-mentioned specific functions of the power management module 1 is specifically as follows: the external energy storage power supply 2 is electrically connected to the main device 5, forming a first power supply circuit for directly supplying power to the main device 5 through the external energy storage power supply 2. A first node a is formed in the first power supply circuit at a position close to the external energy storage power supply 2, and the first power supply circuit is electrically connected to the first battery 3 through the first node a, so that a first charging circuit for charging the first battery 3 is formed between the external energy storage power supply 2 and the first battery 3. The first power supply circuit is electrically connected to the second battery 4 through the first node a, so that a second charging circuit for charging the second battery 4 is formed between the external energy storage power supply 2 and the second battery 4.

For example, the external energy storage power supply 2 can use the 12V DC output of a fully charged Juos 750 W, 500,000 mAh mobile power supply to power the main device 5. The external energy storage power supply 2 can also use the 24V DC output of an ambulance onboard power supply to power the main device 5.

In addition, a second node b is formed in the first power supply circuit at a position close to the main device 5, and the first battery 3 is electrically connected to the second node b, so that a second power supply circuit for supplying power to the main device 5 through the first battery 3 is formed between the first battery 3 and the main device 5. The second battery 4 is electrically connected to the second node b, so that a third power supply circuit for supplying power to the main device 5 through the second battery 4 is formed between the second battery 4 and the main device 5.

Furthermore, the above-mentioned power management circuit includes: 5 MOS switches, which are respectively a first MOS switch 9, a second MOS switch 10, a third MOS switch 11, a fourth MOS switch 12 and a fifth MOS switch 13. The first MOS switch 9 is arranged between the first node a and the second node b, and the second MOS switch 10 is arranged between the first battery 3 and the first node a. The third MOS switch 11 is arranged between the second battery 4 and the first node a. The fourth MOS switch 12 is arranged between the first battery 3 and the second node b. The fifth MOS switch 13 is arranged between the second battery 4 and the second node b.

Furthermore, the gates of the first MOS switch 9, the second MOS switch 10, the third MOS switch 11, the fourth MOS switch 12 and the fifth MOS switch 13 respectively form ENB terminals, and the control signal output terminal of the power management module 1 is respectively connected to the ENB terminals of the first MOS switch 9, the second MOS switch 10, the third MOS switch 11, the fourth MOS switch 12 and the fifth MOS switch 13. In this way, the power management module 1 can control the on and off of the first MOS switch 9, the second MOS switch 10, the third MOS switch 11, the fourth MOS switch 12 and the fifth MOS switch 13 through the control signal. For example, the power management module 1 controls the on of the first MOS switch 9, the second MOS switch 10, the third MOS switch 11, the fourth MOS switch 12 and the fifth MOS switch 13 through the high level signal, and controls the off of the first MOS switch 9, the second MOS switch 10, the third MOS switch 11, the fourth MOS switch 12 and the fifth MOS switch 13 through the low level signal.

In addition, the power management circuit further includes: 3 diodes, which are respectively a first diode 6, a second diode 7 and a third diode 8. The first diode 6 is arranged between the external energy storage power supply 2 and the first node a, the second diode 7 is arranged between the fourth MOS switch 12 and the second node b, and the third diode 8 is arranged between the fifth MOS switch 13 and the second node b.

Furthermore, the external energy storage power supply voltage monitoring unit 101 performs a first real-time monitoring of the external energy storage power supply voltage; if the external energy storage power supply voltage does not meet the first preset condition, the circuit control unit 103 controls the external energy storage power supply 2 to directly power the main device 5, and charges the first battery 3 and the second battery 4 at the same time, and the external energy storage power supply voltage monitoring unit 101 continues to perform a first real-time monitoring of the external energy storage power supply voltage; if the external energy storage power supply voltage meets the first preset condition, the circuit control unit 103 reduces the first charging power duty cycle of the first battery 3 and the second battery 4 according to the first preset ratio.

The circuit control unit 103 records the number of first-stage adjustment times and the corresponding first-stage adjustment time; predicts the next first-stage adjustment time by using the recorded first preset number of first-stage adjustment times and the corresponding first-stage adjustment time; advances the first preset time threshold before the predicted next first-stage adjustment time, and continues to reduce the first charging power duty cycle of the first battery 3 and the second battery 4 according to the first preset ratio.

Compared with the prior art, the power management system for life support equipment provided, for life support equipment, when it is detected that the power of the external energy storage power supply is insufficient to power the whole machine, the charging power of the battery is reduced by adjusting the duty cycle. At the same time, a prediction algorithm is added when adjusting the duty cycle to reduce the probability of the external energy storage power supply triggering overload protection. In this way, when the power of the external energy storage power supply is insufficient, the internal battery can be guaranteed to have more power, thereby improving the endurance of the ECMO device when transferring patients and better protecting the patient's life safety.

Corresponding to the power management system of a life support device disclosed above, further discloses a power management method of a life support device. The following describes in detail the power management method of a life support device in combination with the power management system of a life support device described above.

Figure 3:
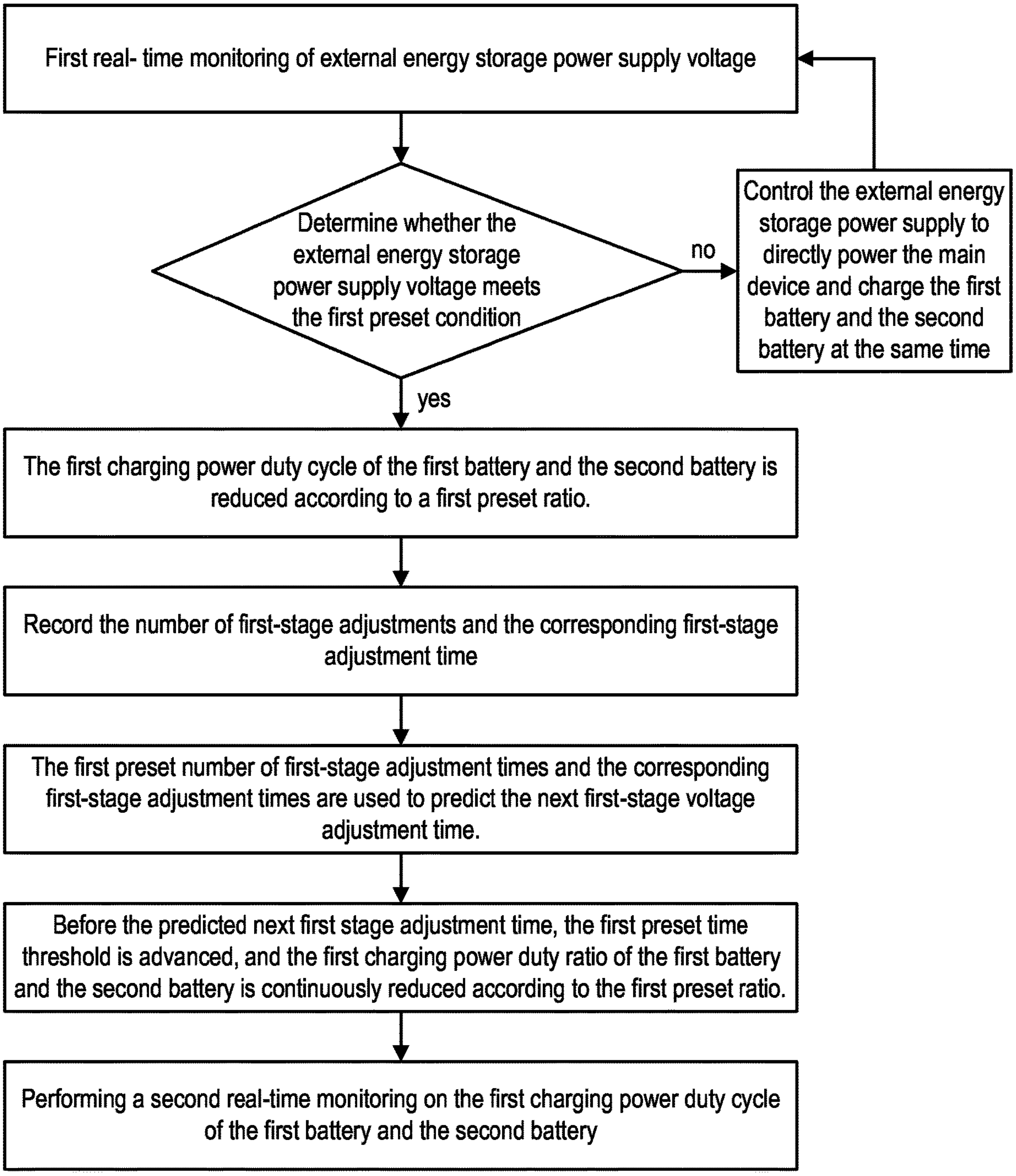
FIG. 3 is a schematic flow chart of a power management method for a life support device provided by an embodiment of the present invention.

As shown in FIG. 3, the specific steps of a power management method for a life support device provided in an embodiment of the present application are described in detail below.

A power management method for a life support device provided in an embodiment of the present application is applied to a power management module 1. The power management module 1 has an MCU (Microcontroller Unit), whose main functions are to monitor the voltage of an external energy storage power supply, monitor the battery power and control the switch circuit. Specifically, the MCU implements the above functions through an external energy storage power supply voltage monitoring unit 101, a battery monitoring unit 102 and a circuit control unit 103.

Figure 4:
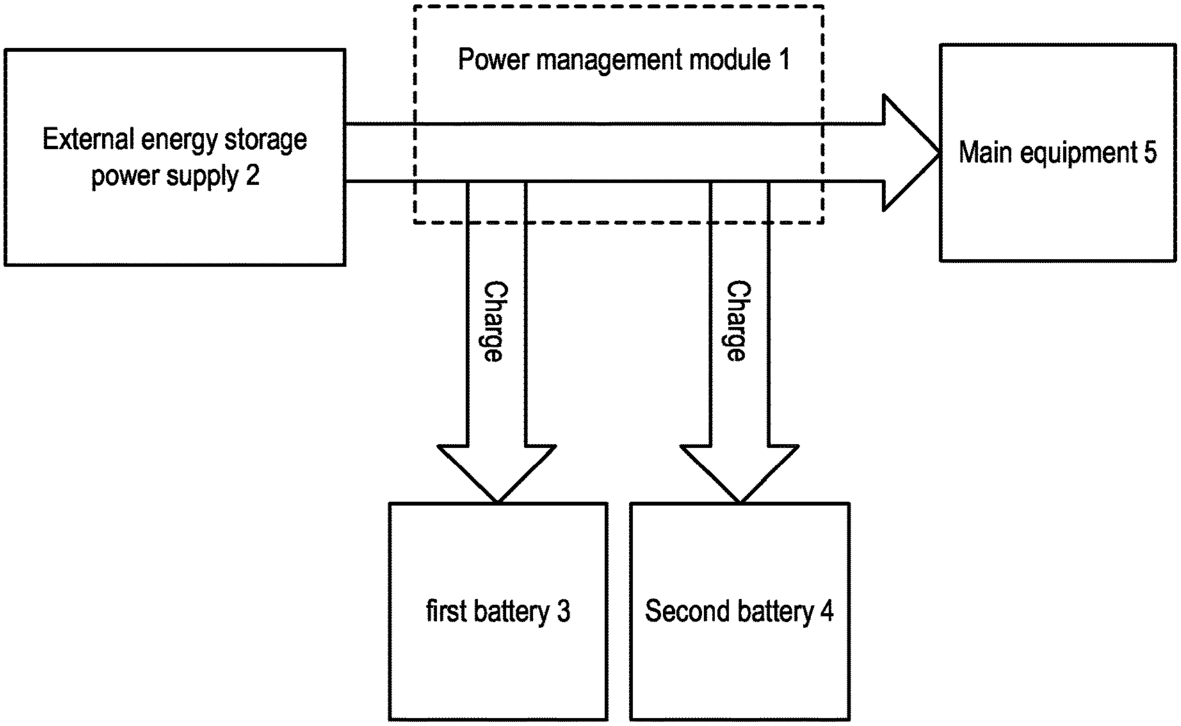
FIG. 4 is a schematic diagram of a circuit principle for controlling an external energy storage power source to directly power a main device and simultaneously charge a first battery and a second battery in a power management method for a life support device provided by an embodiment of the present invention.

The external energy storage power supply voltage monitoring unit 101 monitors the external energy storage power supply voltage inputted externally in real time through ADC analog-to-digital conversion, and the sampling period is 50-200 milliseconds. When the power of the external energy storage power supply is sufficient to power the entire main device 5, a power management circuit operates in accordance with the first power supply mode, as shown in FIG. 4, the external energy storage power supply 2 directly powers the main device 5, and charges the first battery 3 and the second battery 4. At this time, the output power of the external energy storage power supply 2 is equal to the power supply power of the main device 5 plus the charging power of the first battery 3 and the second battery 4.

Specifically, the external energy storage power supply voltage monitoring unit 101 performs a first real-time monitoring on the external energy storage power supply voltage. If the external energy storage power supply voltage does not meet the first preset condition, the circuit control unit 103 controls the external energy storage power supply 2 to directly supply power to the main device 5, and charges the first battery 3 and the second battery 4 at the same time, and the external energy storage power supply voltage monitoring unit 101 continues to perform a first real-time monitoring on the external energy storage power supply voltage.

When the voltage of the external energy storage power supply 2 does not meet the first preset condition, the circuit control unit 103 controls the first MOS switch 9, the second MOS switch 10 and the third MOS switch 11 to be turned on, and the fourth MOS switch 12 and the fifth MOS switch 13 to be turned off. At this time, the external energy storage power supply 2 directly supplies power to the main device 5, and the external energy storage power supply 2 charges both the first battery 3 and the second battery 4 at the same time.

Further, the external energy storage power supply voltage monitoring unit 101 performs a first real-time monitoring of the external energy storage power supply voltage using a first preset condition, that is, the first preset condition is used to determine whether the power of the external energy storage power supply is sufficient to supply power to the entire main device 5. The first preset condition is set as the external energy storage power supply voltage being lower than a first preset threshold value for a continuous first time period, the first time period being 500 milliseconds to 1000 milliseconds, and the first preset threshold being 90% to 95% of a normal value of the external energy storage power supply voltage.

When in the first power supply mode, when it is found through the above-mentioned first real-time monitoring that the power of the external energy storage power supply is insufficient to supply power to the entire main device 5, the external energy storage power supply 2 still directly supplies power to the main device 5, and reduces the power duty cycle of charging the two batteries to adjust the power, thereby ensuring that the external energy storage power supply 2 continues to supply power to the main device 5 normally.

Specifically, if the voltage of the external energy storage power supply meets the first preset condition, the circuit control unit 103 reduces the first charging power duty cycle of the first battery 3 and the second battery 4 according to the first preset ratio. Further, the first preset ratio can be set to 2% of the first charging power duty cycle, that is, each time the voltage of the external energy storage power supply meets the first preset condition, the first charging power duty cycle of the first battery 3 and the second battery 4 is reduced by 2%.

Referring to FIG. 3, in an embodiment of the present invention, a prediction algorithm is added when adjusting the duty cycle to reduce the probability of triggering overload protection by the power of the external energy storage power supply. Specifically, the above prediction algorithm is implemented by the circuit control unit 103 executing the following steps: recording the number of first-stage adjustments and the corresponding first-stage adjustment time; using the first preset number of first-stage adjustment times and the corresponding first-stage adjustment time recorded, predicting the next first-stage adjustment time; before the predicted next first-stage adjustment time, the first preset time threshold is advanced, and the first charging power duty cycle of the first battery 3 and the second battery 4 is continuously reduced according to the first preset ratio.

Compared with the prior art, the power management method for life support equipment provided is for life support equipment. When it is detected that the power of the external energy storage power supply is insufficient to power the whole device, the charging power of the battery is reduced by adjusting the duty cycle. At the same time, a prediction algorithm is added when adjusting the duty cycle to reduce the probability of the external energy storage power supply triggering overload protection. In this way, when the power of the external energy storage power supply is insufficient, the internal battery can be guaranteed to have more power, thereby improving the endurance of the ECMO device when transferring patients and better protecting the patient's life safety.

Furthermore, the first preset number may be set to 5 times, and the first preset time threshold may be set to 5 seconds. Thus, as described above, the recorded adjustment times of each first-stage and the corresponding adjustment time of the first-stage are specifically as follows: the first charging power duty cycle of the first battery 3 and the second battery 4 is reduced from 100% to 98%, that is, the closing duty cycle of the second MOS switch 10 and the third MOS switch 11 is reduced from 100% to 98%, the first-stage adjustment times are recorded as the first time, and the corresponding first-stage adjustment time is recorded as T1; the first charging power duty cycle of the first battery 3 and the second battery 4 is reduced from 98% to 96%, that is, the closing duty cycle of the second MOS switch 10 and the third MOS switch 11 is reduced from 98% to 96%, the first-stage adjustment times are recorded as the second time, and the corresponding first-stage adjustment time is recorded as T2; the first charging power duty cycle of the first battery 3 and the second battery 4 is reduced from 96% to 94%, that is, the closing duty cycle of the second MOS switch 10 and the third MOS switch 11 is reduced from 96% to 94%, record the number of first-stage adjustments as the third time, and record the corresponding first-stage adjustment time as T3; the first charging power duty cycle of the first battery 3 and the second battery 4 is reduced from 94% to 92%, that is, the closing duty cycle of the second MOS switch 10 and the third MOS switch 11 is reduced from 94% to 92%, record the number of first-stage adjustments as the fourth time, and record the corresponding first-stage adjustment time as T4; the first charging power duty cycle of the first battery 3 and the second battery 4 is reduced from 92% to 90%, that is, the closing duty cycle of the second MOS switch 10 and the third MOS switch 11 is reduced from 92% to 90%, record the number of first-stage adjustments as the fifth time, and record the corresponding first-stage adjustment time as T5.

Figure 5:
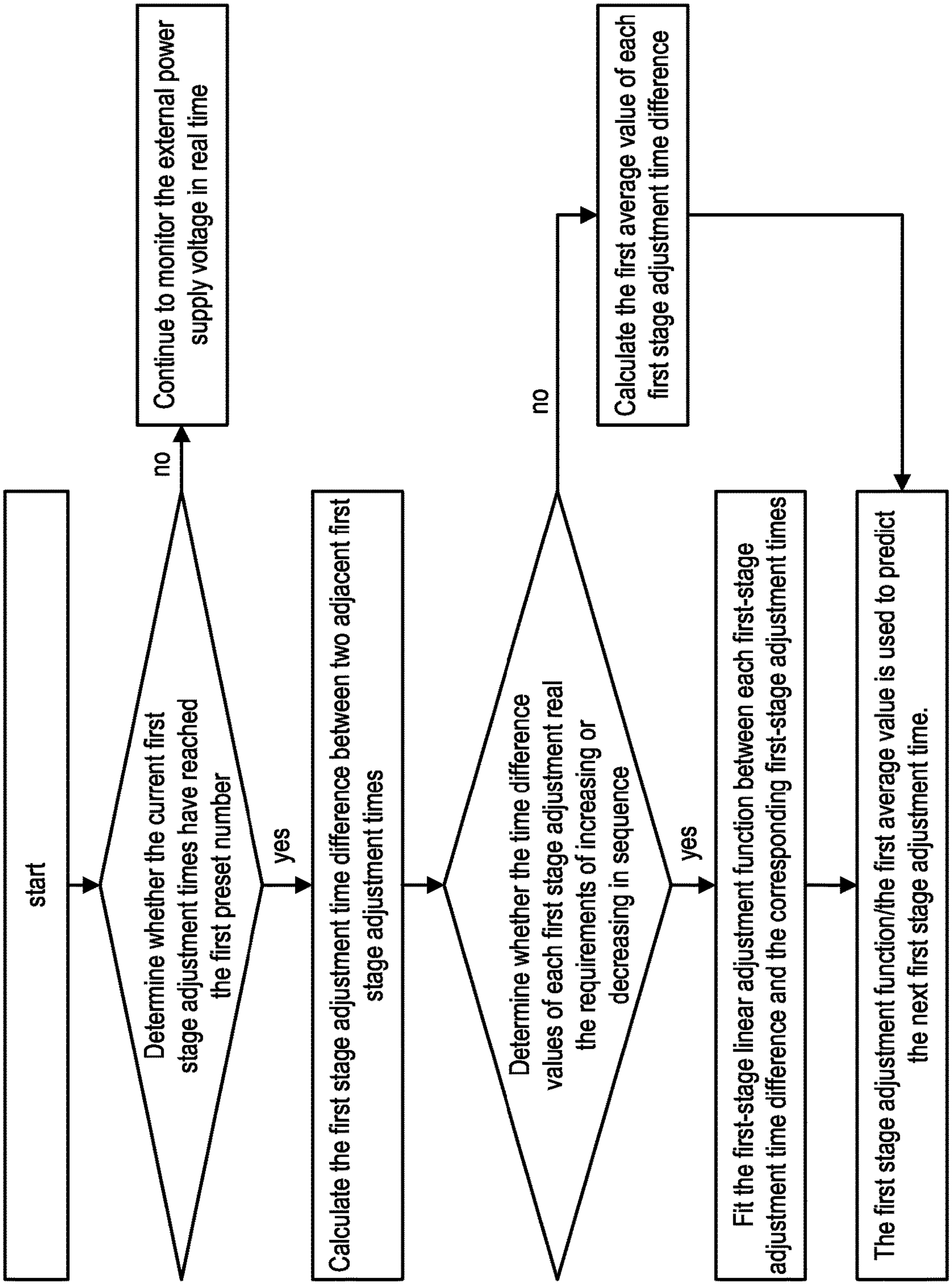
FIG. 5 is a schematic flow chart of predicting the next first-stage adjustment time by using a first preset number of first-stage adjustment times and corresponding first-stage adjustment times recorded in a power management method for a life support device provided by an embodiment of the present invention.

Referring to FIG. 5, further, based on the prediction algorithm, the steps of predicting the next first-stage adjustment time using the recorded first-stage adjustment times and the corresponding first-stage adjustment times are as follows: determine whether the current first-stage adjustment times reach the first preset number; if the current first-stage adjustment times do not reach the first preset number, continue to perform the first real-time monitoring of the external energy storage power supply voltage; if the current first-stage adjustment times reach the first preset number, calculate the first-stage adjustment time difference between two adjacent first-stage adjustment times in sequence; determine whether each first-stage adjustment time difference satisfies the sequential increase or decrease; if each first-stage adjustment time difference satisfies the sequential increase or decrease, fit the first-stage linear adjustment function between each first-stage adjustment time difference and the corresponding first-stage adjustment times; if each first-stage adjustment time difference does not satisfy the sequential increase or decrease, calculate the first average value of each first-stage adjustment time difference; use the first-stage adjustment function/first average value to predict the next first-stage adjustment time.

More specifically, based on the prediction algorithm, as described above, when the first preset number is set to 5 times, the specific steps of predicting the next first-stage adjustment time using the 5 recorded first-stage adjustment times and the corresponding first-stage adjustment times are as follows: judging whether the current first-stage adjustment number reaches 5 times; if the current first-stage adjustment number does not reach 5 times, continuing to perform the first real-time monitoring of the external energy storage power supply voltage; if the current first-stage adjustment number reaches 5 times, calculating the first-stage adjustment time difference between two adjacent first-stage adjustment times in sequence, As described above, the difference ΔT1 between time point T2 and time point T1, the difference ΔT2 between time point T3 and time point T2, the difference ΔT3 between time point T4 and time point T3, and the difference ΔT4 between time point T5 and time point T4 are calculated in sequence; whether the above first-stage adjustment time differences ΔT1, ΔT2, ΔT3, and ΔT4 satisfy the requirements of increasing or decreasing in sequence; if the above first-stage adjustment time differences ΔT1, ΔT2, ΔT3, and ΔT4 satisfy the requirements of increasing or decreasing in sequence, the first-stage linear adjustment function between the above first-stage adjustment time differences Δ T1, ΔT2, ΔT3, and ΔT4 and the corresponding first-stage adjustment times 1, 2, 3, and 4 is fitted using the least squares method, and the first formula for fitting the first-stage linear adjustment function is as follows:

$$\triangle Tm = k1 \cdot m + b1$$

Wherein, m is the number of first-stage adjustment times, $\Delta Tm$ is the first-stage adjustment time difference corresponding to the first-stage adjustment times, k1 is the first slope, and b1 is the first intercept;

The first-stage adjustment function is used to predict the next first-stage adjustment time difference. For example, if m=5, the formula of the first-stage linear adjustment function can be used to predict the first-stage adjustment time difference ΔT5 corresponding to the fifth first-stage adjustment. In this way, according to the following second formula:

$$T(m+1) = Tm + \triangle Tm$$

Assuming m=5, the next first-stage adjustment time corresponding to the fifth first-stage adjustment can be calculated, that is, the first-stage adjustment time T6 corresponding to the sixth first-stage adjustment.

If the above first-stage adjustment time differences ΔT1, ΔT2, ΔT3, ΔT4 do not satisfy the requirement of increasing or decreasing in sequence, then the first average value AVEΔT4 of the first-stage adjustment time differences ΔT1, ΔT2, ΔT3, ΔT4 is calculated; and the next first-stage adjustment time is predicted using the first average value according to the following third formula:

$$T(m+1) = Tm + AVE\Delta T(m-1)$$

Wherein, m is the number of first-stage adjustments, and AVEΔT (m−1) is the first average value of the first-stage adjustment time differences corresponding to each first-stage adjustment time when the number of first-stage adjustments is m−1;

Let m=5, that is, T6=T5+AVEΔT4.

Figure 7:
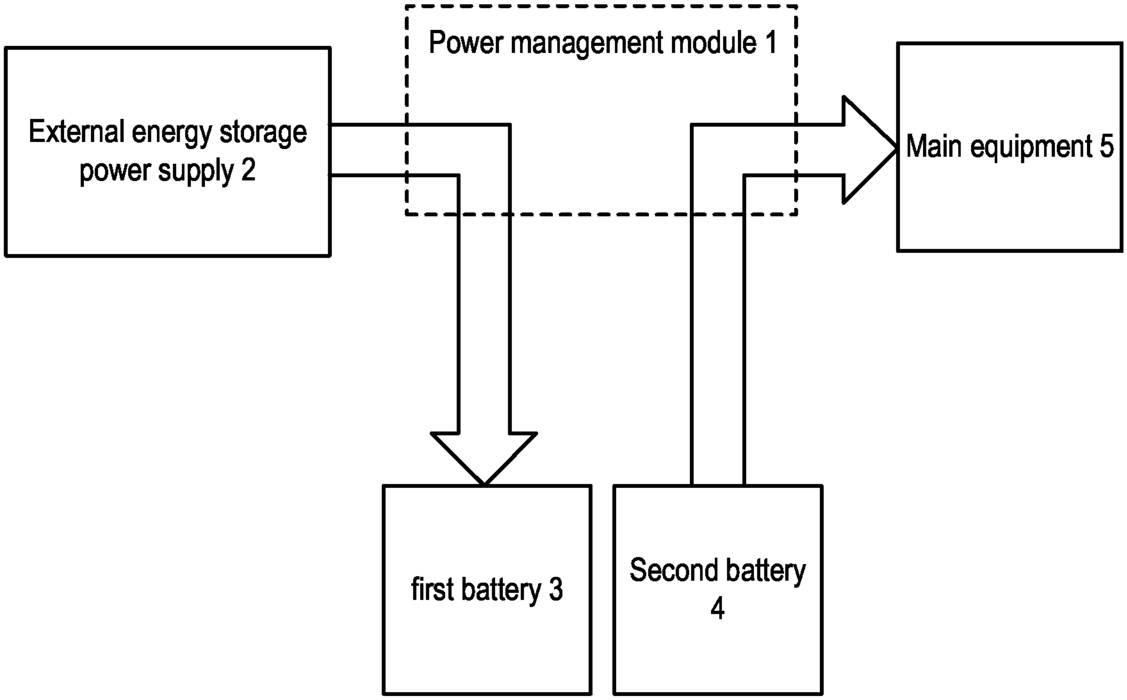
FIG. 7 is a schematic diagram of the circuit principle of switching the power supply battery to power the main device and controlling the external energy storage power supply to charge only the rechargeable battery in a power management method for a life support device provided by an embodiment of the present invention.

Continuing, when the first charging power duty cycle of the first battery 3 and the second battery 4 is reduced to 0, and the first battery 3 or the second battery 4 has a certain amount of power, a working mode of a power management circuit is switched to a second power supply mode, as shown in FIG. 7, the main device 5 is powered by the battery with a high power, and the external energy storage power supply 2 charges the battery with a low power. At this time, because the external energy storage power supply 2 only needs to charge one battery, the overload protection will not be triggered prematurely due to overcurrent.

Figure 6:
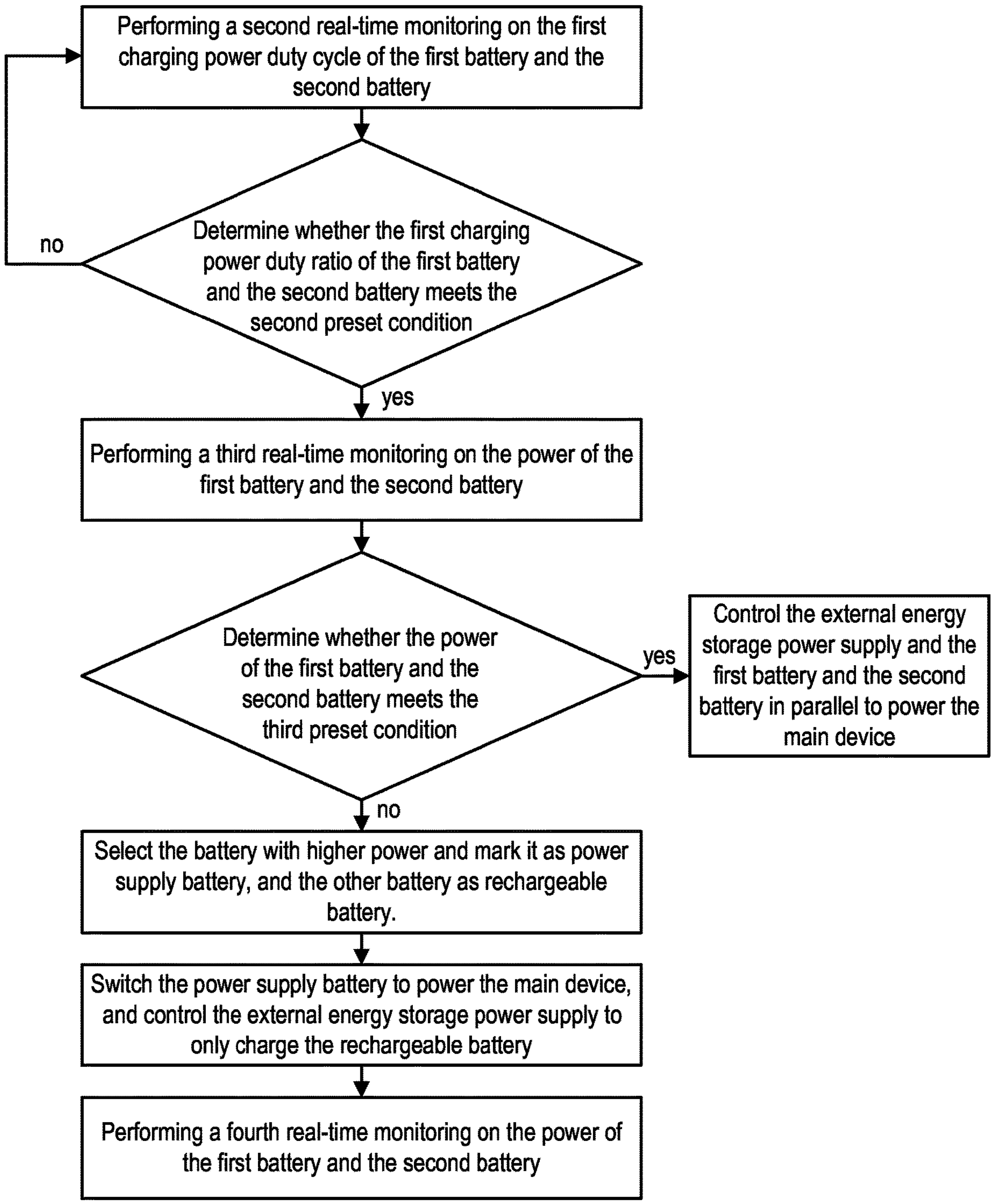
FIG. 6 is a schematic flow chart of another power management method for life support equipment provided by an embodiment of the present invention.

Specifically, in combination with FIG. 3 and FIG. 6, after the first charging power duty cycle of the first battery 3 and the second battery 4 is lowered each time, the battery monitoring unit 102 performs a second real-time monitoring on the first charging power duty cycle of the first battery 3 and the second battery 4.

In the embodiment of the present invention, the second real-time monitoring is implemented by using the second preset condition, that is, the second preset condition is set as the first charging power duty cycle of the first battery and the second battery is reduced to 0.

If the first charging power duty ratio of the first battery 3 and the second battery 4 does not satisfy the second preset condition, the battery monitoring unit 102 continues to perform second real-time monitoring on the first charging power duty ratio of the first battery 3 and the second battery 4.

If the first charging power duty ratios of the first battery 3 and the second battery 4 meet the second preset condition, the battery monitoring unit 102 performs a third real-time monitoring on the power levels of the first battery 3 and the second battery 4.

Specifically, the third real-time monitoring is realized by utilizing the third preset condition, and the third preset condition is set as that the first power value of the first battery 3 and the second power value of the second battery 4 do not reach their respective corresponding second preset thresholds, and the second preset thresholds corresponding to the first battery 3 and the second battery 4 are 1%-5% of their own power respectively.

If the power levels of the first battery 3 and the second battery 4 do not meet the third preset condition, the circuit control unit 103 selects the battery with higher power level as the power supply battery and marks the other battery as the rechargeable battery; switches the power supply battery to power the main device, and controls the external energy storage power supply 2 to only charge the rechargeable battery.

As described above, when the power of the first battery 3 and the second battery 4 does not meet the third preset condition, if the power of the first battery 3 is higher, the first battery 3 is marked as a power supply battery, and the second battery 4 is marked as a charging battery. In conjunction with FIG. 2, at this time, the circuit control unit 103 controls the third MOS switch 11 and the fourth MOS switch 12 to be turned on, and the first MOS switch 9, the second MOS switch 10 and the fifth MOS switch 13 are turned off. At this time, the first battery 3 is switched to supply power to the main device 5, and the external energy storage power supply 2 only charges the second battery 4.

Figure 8:
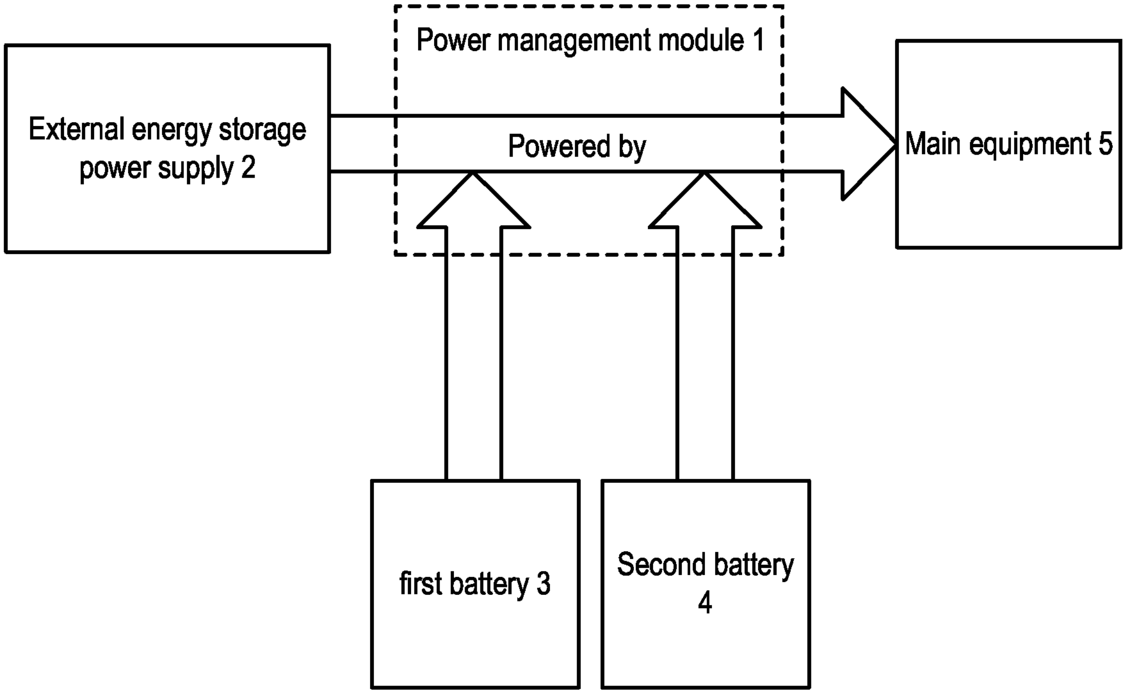
FIG. 8 is a schematic diagram of a circuit principle for controlling an external energy storage power source and a first battery and a second battery to be connected in parallel to supply power to a main device in a power management method for a life support device provided by an embodiment of the present invention.

If the power of the first battery 3 and the second battery 4 meets the third preset condition, the circuit control unit 103 controls the external energy storage power supply 2 and the first battery 3 and the second battery 4 to be connected in parallel to supply power to the main device 5. That is, the working mode of a power management circuit is switched to the third power supply mode, as shown in FIG. 8, the main device 5 is jointly powered by the external energy storage power supply 2, the first battery 3 and the second battery 4. When the power levels of the first battery 3 and the second battery 4 meet the third preset condition, the circuit control unit 103 controls the first MOS switch 9, the fourth MOS switch 12 and the fifth MOS switch 13 to be turned on, and the second MOS switch 10 and the third MOS switch 11 to be turned off. At this time, the external energy storage power supply 2, the first battery 3 and the second battery 4 are connected in parallel to supply power to the main device 5.

Compared with the prior art, the power management method for a life support device reduces the duty cycle of the charging power of the two batteries for the life support device when it is detected that the power of the external energy storage power supply 2 is insufficient to power the whole device; when the duty cycle of the charging power of the two batteries is reduced to 0, the power of the two batteries is detected, and when the power of one of the batteries is sufficient to power the device, the high-power battery is immediately switched to power the device, and at the same time, the external energy storage power supply 2 continues to charge the low-power battery; when the power of both batteries is insufficient to power the device, the circuit is directly switched to the external energy storage power supply 2 and the two batteries in parallel to power the device. In this way, when the external energy storage power supply 2 is insufficient in power, the external energy storage power supply 2 can be prevented from triggering the overload protection too early and cutting off the power, and the external energy storage power supply 2 and the two batteries 3, 4 can be used as much as possible to continue to power the device, thereby improving the battery life of the ECMO device and better protecting the patient's life safety.

In an embodiment of the present invention, after a working mode of a power management circuit is switched to a second power supply mode, in this mode, it is necessary to maintain the power balance of two batteries.

Further, if the power levels of the first battery 3 and the second battery 4 do not satisfy the third preset condition, a fourth real-time monitoring is performed on the power levels of the first battery 3 and the second battery 4.

Referring to FIG. 6, preferably, when the power levels of the first battery 3 and the second battery 4 do not meet the third preset condition, the circuit control unit 103 selects a battery with a higher power level and marks it as a power supply battery, and the other battery is marked as a rechargeable battery; after switching the power supply battery to power the main device and controlling the external energy storage power supply 2 to only charge the rechargeable battery, a fourth real-time monitoring of the power levels of the first battery 3 and the second battery 4 is performed.

Specifically, in the embodiment of the present invention, the fourth real-time monitoring is implemented by utilizing the fourth preset condition, and the fourth preset condition is set as one of the first power value of the first battery 3 and the second power value of the second battery 4 exceeds their respective corresponding third preset thresholds, and the third preset thresholds corresponding to the first battery 3 and the second battery 4 are respectively greater than or equal to 3% and less than or equal to 8% of their own power.

If the power levels of the first battery 3 and the second battery 4 meet the fourth preset condition, a fifth real-time monitoring is performed on the power levels of the current power supply battery and the current charging battery.

Specifically, in an embodiment of the present invention, the fifth real-time monitoring is implemented using the fifth preset condition, and the fifth preset condition is set to a first preset ratio in which the power value of the current power supply battery is less than the power value of the current charging battery, and the first preset ratio is 92%-97%.

If the power levels of the current power supply battery and the current charging battery do not meet the fifth preset condition, the fourth real-time monitoring of the power levels of the first battery 3 and the second battery 4 continues.

If the power levels of the current power supply battery and the current rechargeable battery meet the fifth preset condition, reselect the battery with higher power level as the power supply battery, and mark the other battery as the rechargeable battery; switch the updated power supply battery to power the main device, control the external energy storage power supply 2 to charge only the updated rechargeable battery, and continue to perform the fourth real-time monitoring of the power levels of the first battery 3 and the second battery 4.

As described above, if the power of the current power supply battery (first battery 3) and the current charging battery (second battery 4) meets the fifth preset condition, the second battery 4 is updated to be marked as a power supply battery, and the first battery 3 is updated to be marked as a charging battery. In conjunction with FIG. 2, at this time, the circuit control unit 103 controls the second MOS switch 10 and the fifth MOS switch 13 to be turned on, and the first MOS switch 9, the third MOS switch 11 and the fourth MOS switch 12 are turned off. At this time, the second battery 4 is switched to supply power to the main device 5, and the external energy storage power supply 2 only charges the first battery 3.

If the power levels of the first battery 3 and the second battery 4 do not satisfy the fourth preset condition, a sixth real-time monitoring is performed on the power levels of the current power supply battery and the current charging battery.

Specifically, in an embodiment of the present invention, the sixth real-time monitoring is implemented using the sixth preset condition, and the sixth preset condition is set to a second preset ratio in which the power value of the current power supply battery is less than the power value of the current charging battery, and the second preset ratio is 99%-99.7%.

If the power levels of the current power supply battery and the current charging battery do not meet the sixth preset condition, the fourth real-time monitoring of the power levels of the first battery 3 and the second battery 4 continues.

If the power levels of the current power supply battery and the current rechargeable battery meet the sixth preset condition, the battery with higher power level is reselected and marked as the power supply battery, and the other battery is marked as the rechargeable battery; the updated power supply battery is switched to power the main device 5, the external energy storage power supply 2 is controlled to charge only the updated rechargeable battery, and the fourth real-time monitoring of the power levels of the first battery 3 and the second battery 4 is continued.

As described above, if the power of the current power supply battery (first battery 3) and the current charging battery (second battery 4) meets the sixth preset condition, the second battery 4 is updated to be marked as a power supply battery, and the first battery 3 is updated to be marked as a charging battery. In conjunction with FIG. 2, at this time, the circuit control unit 103 controls the second MOS switch 10 and the fifth MOS switch 13 to be turned on, and the first MOS switch 9, the third MOS switch 11 and the fourth MOS switch 12 are turned off. At this time, the second battery 4 is switched to supply power to the main device 5, and the external energy storage power supply 2 only charges the first battery 3.

When the power of the external energy storage power source 2 is insufficient to charge a single battery, the duty cycle of the corresponding battery charging is reduced to adjust the power.

Further, if the power levels of the first battery 3 and the second battery 4 do not satisfy the fourth preset condition, a seventh real-time monitoring is performed on the external energy storage power supply voltage.

Figure 9:
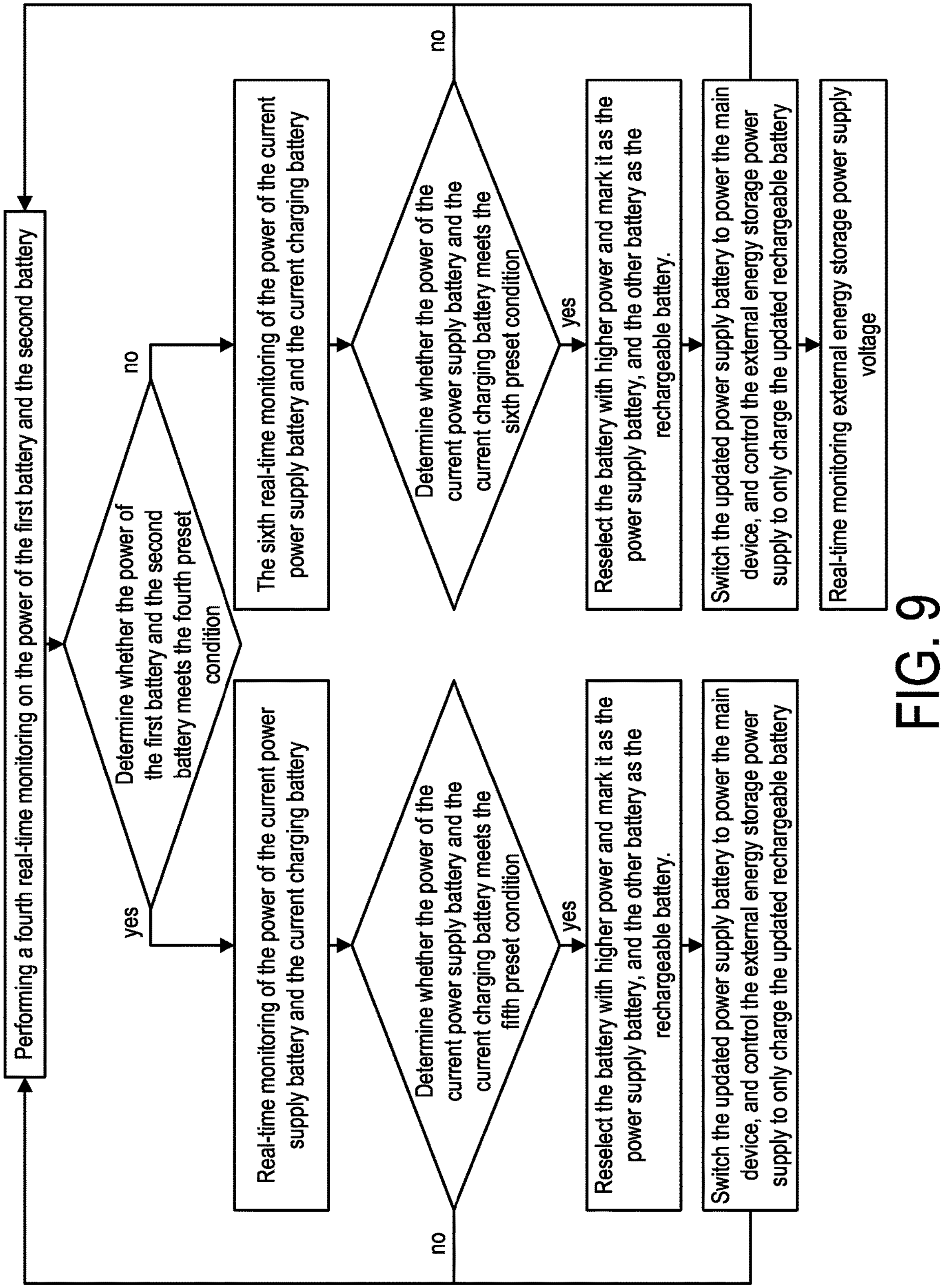
FIG. 9 is a schematic flow chart of another power management method for life support equipment provided by an embodiment of the present invention.
Figure 10:
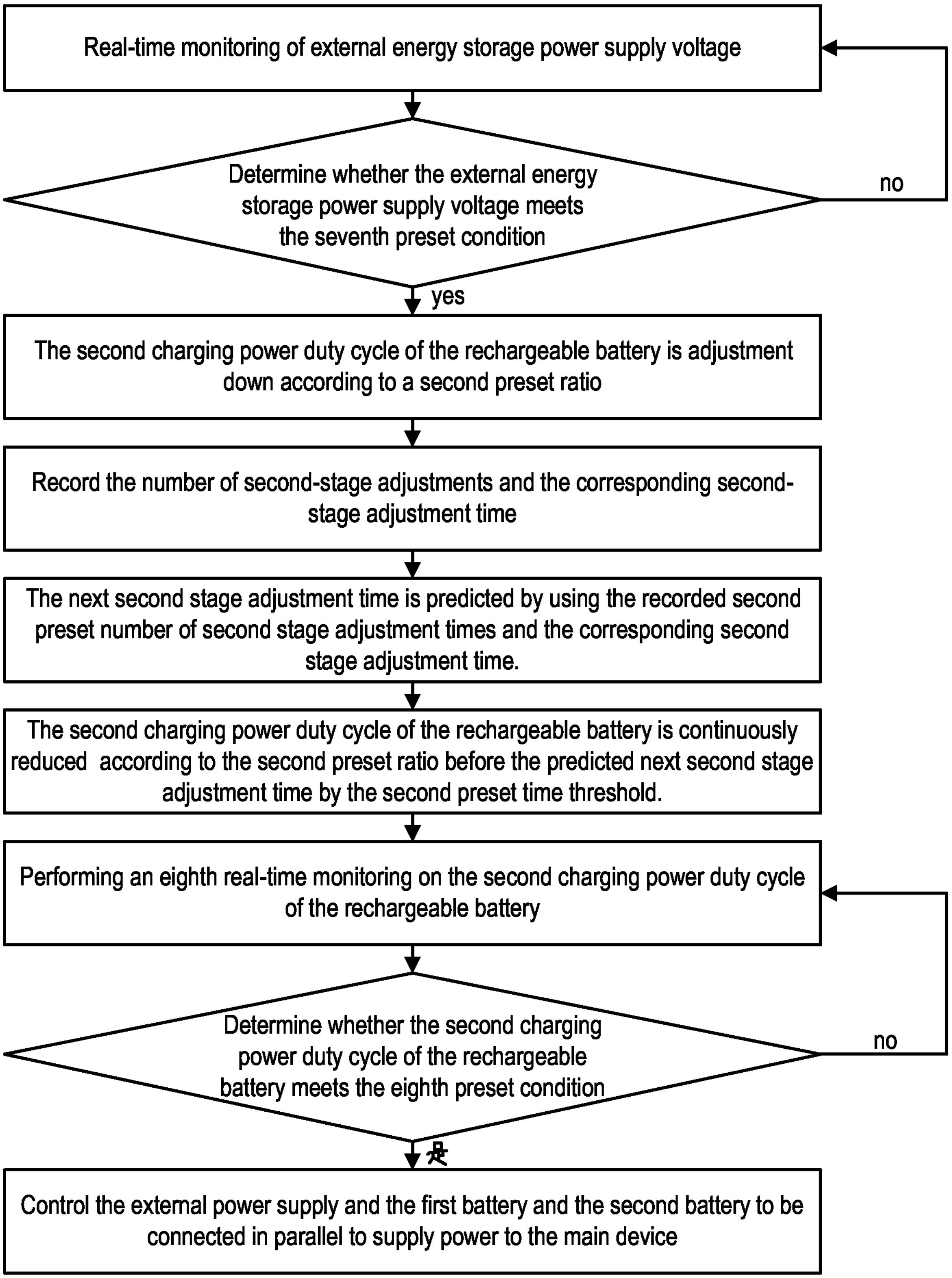
FIG. 10 is a schematic flow chart of another power management method for life support equipment provided by an embodiment of the present invention.

Referring to FIG. 9, preferably, if the power levels of the current power supply battery and the current rechargeable battery meet the sixth preset condition, the circuit control unit 103 selects the battery with higher power level as the power supply battery and marks the other battery as the rechargeable battery; switches the power supply battery to power the main device, and controls the external energy storage power supply 2 to only charge the rechargeable battery, and then performs the seventh real-time monitoring of the external energy storage power supply voltage.

Specifically, in an embodiment of the present invention, a seventh real-time monitoring is implemented using a seventh preset condition, and the seventh preset condition is set as the external energy storage power supply voltage is lower than the fourth preset threshold value for a second consecutive time period, the second time period is greater than or equal to 100 milliseconds and less than or equal to 200 milliseconds, and the fourth preset threshold value is greater than or equal to 96% of the normal value of the external energy storage power supply voltage and less than or equal to 98% of the normal value of the external energy storage power supply voltage.

If the voltage of the external energy storage power supply 2 does not meet the seventh preset condition, the seventh real-time monitoring of the voltage of the external energy storage power supply continues.

If the external energy storage power supply voltage meets the seventh preset condition, the circuit control unit 103 adjusts the second charging power duty cycle of the rechargeable battery down according to the second preset ratio. Further, the second preset ratio can be set to 2% of the second charging power duty cycle, that is, each time the external energy storage power supply voltage meets the seventh preset condition, the first charging power duty cycle of the rechargeable battery is adjusted down by 2%.

In an embodiment of the present invention, a prediction algorithm is added when adjusting the duty cycle to reduce the probability of triggering overload protection by the power of the external energy storage power supply 2. Specifically, the above prediction algorithm is implemented by the circuit control unit 103 executing the following steps: recording the number of second-stage adjustments and the corresponding second-stage adjustment time; using the second preset number of second-stage adjustment times and the corresponding second-stage adjustment time recorded, predicting the next second-stage adjustment time; advancing the second preset time threshold before the predicted next second-stage adjustment time, and continuing to reduce the second charging power duty cycle of the rechargeable battery according to the second preset ratio.

Furthermore, the second preset number may be set to 5 times, and the second preset time threshold may be set to 5 seconds. Thus, as described above, if the first battery 3 is being charged at this time, the recorded second-stage adjustment times and the corresponding second-stage adjustment times are specifically as follows: the second charging power duty cycle of the first battery 3 is reduced from 100% to 98%, that is, the closing duty cycle of the second MOS switch 10 is reduced from 100% to 98%, the second-stage adjustment times are recorded as the first time, and the corresponding second-stage adjustment time is recorded as t1; the first charging power duty cycle of the first battery 3 is reduced from 98% to 96%, that is, the closing duty cycle of the second MOS switch 10 is reduced from 98% to 96%, the second-stage adjustment times are recorded as the second time, and the corresponding second-stage adjustment time is recorded as t2; the second charging power duty cycle of the first battery 3 is reduced from 96% to 94%, that is, the closing duty cycle of the second MOS switch 10 is reduced from 96% to 94%, the second-stage adjustment times are recorded as the third time, and the corresponding second-stage adjustment time is recorded as t3; the second charging power duty cycle of the first battery 3 is reduced from 94% to 92%, that is, the closing duty cycle of the second MOS switch 10 is reduced from 94% to 92%, the second-stage adjustment number is recorded as the 4th time, and the corresponding second-stage adjustment time is recorded as t4; the first charging power duty cycle of the first battery 3 is reduced from 92% to 90%, that is, the closing duty cycle of the second MOS switch 10 is reduced from 92% to 90%, the second-stage adjustment number is recorded as the 5th time, and the corresponding second-stage adjustment time is recorded as t5.

Figure 11:
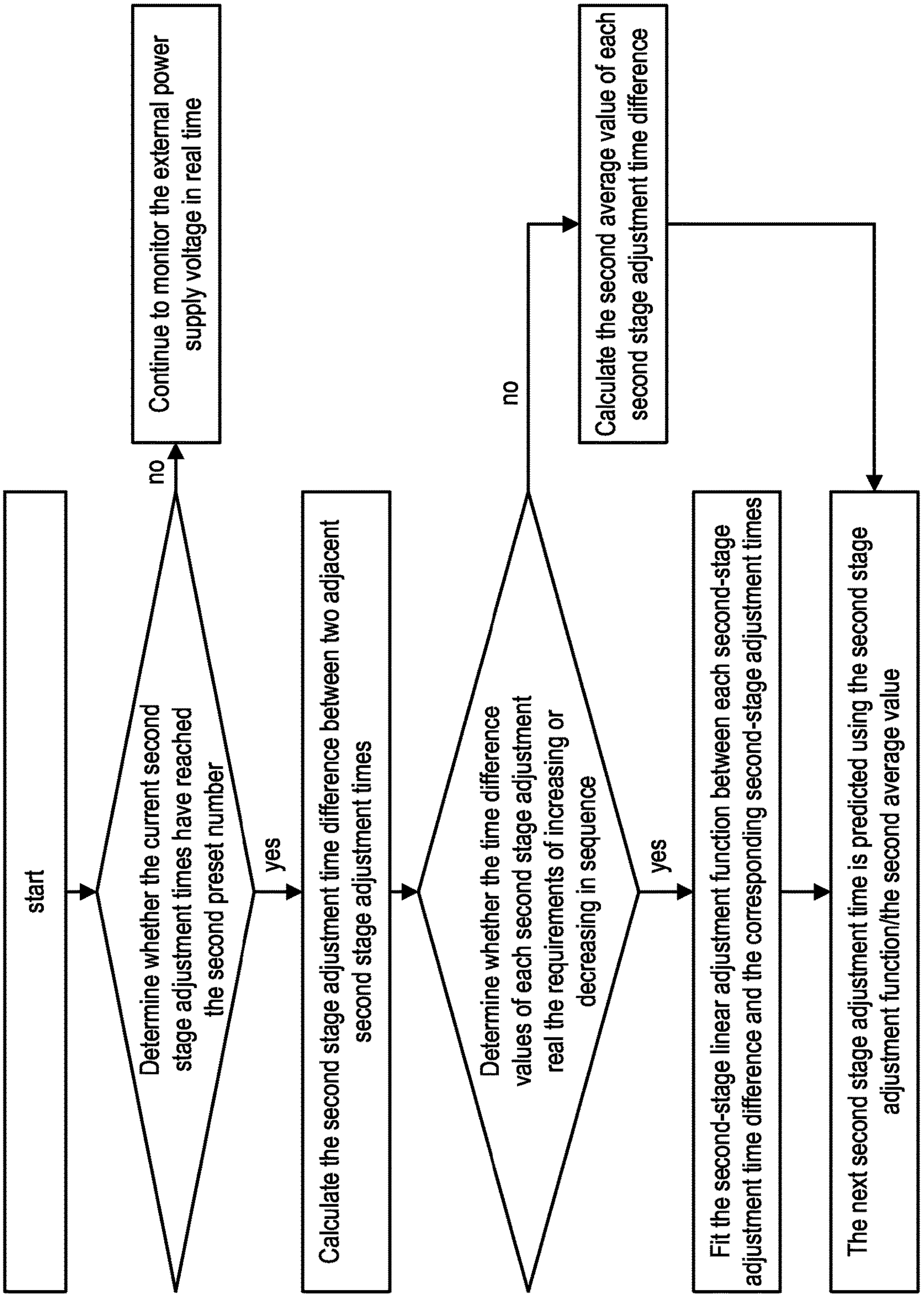
FIG. 11 is a schematic flow chart of predicting the next second-stage adjustment time by using a second preset number of second-stage adjustment times and corresponding second-stage adjustment times recorded in a power management method for a life support device provided by an embodiment of the present invention.

Referring to FIG. 11, further, based on the prediction algorithm, the steps of predicting the next second-stage adjustment time using the recorded second preset number of each second-stage adjustment number and the corresponding second-stage adjustment time are as follows: determine whether the current second-stage adjustment number reaches the second preset number; if the current second-stage adjustment number does not reach the second preset number, continue to perform the seventh real-time monitoring of the external energy storage power supply voltage; if the current second-stage adjustment number reaches the second preset number, calculate the second-stage adjustment time difference between two adjacent second-stage adjustment times in sequence; determine whether each second-stage adjustment time difference satisfies the requirement of increasing or decreasing in sequence; if each second-stage adjustment time difference satisfies the requirement of increasing or decreasing in sequence, fit the second-stage linear adjustment function between each second-stage adjustment time difference and the corresponding second-stage adjustment number; if each second-stage adjustment time difference does not satisfy the requirement of increasing or decreasing in sequence, calculate the second average value of each second-stage adjustment time difference; and predict the next second-stage adjustment time using the second-stage adjustment function/second average value.

More specifically, based on the prediction algorithm in the embodiment of the present invention, as described above, when the second preset number is set to 5 times, the specific steps of predicting the next second-stage adjustment time using the 5 recorded second-stage adjustment times and the corresponding second-stage adjustment time are as follows: determine whether the current second-stage adjustment number has reached 5 times; if the current second-stage adjustment number has not reached 5 times, continue to perform the seventh real-time monitoring of the external energy storage power supply voltage; if the current second-stage adjustment number has reached 5 times, calculate the second-stage adjustment time difference between two adjacent second-stage adjustment times in sequence, as described above, that is, calculate the difference Δt1 between time point t2 and time point t1, time point t3 and time point t4 in sequence. The difference Δt2 between time point t4 and time point t3, the difference Δt3 between time point t5 and time point t4, and the difference Δt4 between time point t5 and time point t4; determine whether the above second-stage adjustment time differences Δt1, Δt2, Δt3, and Δt4 satisfy the requirements of increasing or decreasing in sequence; if the above second-stage adjustment time differences Δt1, Δt2, Δt3, and Δt4 satisfy the requirements of increasing or decreasing in sequence, then use the least squares method to fit the above second-stage adjustment time differences Δt1, Δt2, Δt3, and Δt4 and the corresponding second-stage adjustment times 1, 2, 3, and 4. The fourth formula for fitting the second-stage linear adjustment function is as follows:

$$\Delta tn = k2 \cdot n + b2$$

Wherein, n is the number of second-stage adjustments, $\Delta tn$ is the second-stage adjustment time difference corresponding to the second-stage adjustment number, k2 is the second slope, and b2 is the second intercept;

The second-stage adjustment function is used to predict the next second-stage adjustment time difference. For example, if n=5, the second-stage adjustment time difference $\Delta t5$ corresponding to the fifth second-stage adjustment can be predicted using the formula of the second-stage linear adjustment function. In this way, according to the following fifth formula:

$$t(n+1) = tn + \Delta tn$$

Assuming n=5, the next second-stage adjustment time corresponding to the fifth second-stage adjustment can be calculated, that is, the second-stage adjustment time t6 corresponding to the sixth second-stage adjustment can be calculated.

If the above second-stage adjustment time differences $\Delta t1$, $\Delta t2$, $\Delta t3$, $\Delta t4$ do not satisfy the requirement of increasing or decreasing in sequence, then calculate the second average value AVE$\Delta t4$ of the second-stage adjustment time differences $\Delta t1$, $\Delta t2$, $\Delta t3$, $\Delta t4$; and predict the next second-stage adjustment time using the second average value according to the following sixth formula:

$$t(n+1) = tn + AVE\Delta t(n-1)$$

Wherein, n is the number of second-stage adjustments, and AVE$\Delta t$ (n−1) is the second average value of the second-stage adjustment time differences corresponding to each second-stage adjustment time difference when the number of second-stage adjustments is n−1;

Let n=5, that is, t6=t5+AVE$\Delta$t4.

Continuing, when the power duty cycle of charging a single battery is reduced to 0, the working mode of a power management circuit is switched to a third power supply mode, as shown in FIG. 8, and the main device 5 is powered by an external energy storage power supply 2, a first battery 3 and a second battery 4.

Specifically, the second charging power duty cycle of the rechargeable battery is monitored in eighth real time. The eighth real-time monitoring is implemented by using an eighth preset condition, and the eighth preset condition is set as the second charging power duty cycle of the rechargeable battery is reduced to 0.

If the second charging power duty cycle of the rechargeable battery does not meet the eighth preset condition, the eighth real-time monitoring of the second charging power duty cycle of the rechargeable battery continues.

If the second charging power duty cycle of the rechargeable battery meets the eighth preset condition, the external energy storage power supply 2 and the first battery 3 and the second battery 4 are controlled to be connected in parallel to supply power to the main device 5.

When the second charging power duty cycle of the rechargeable battery meets the eighth preset condition, the circuit control unit 103 controls the first MOS switch 9, the fourth MOS switch 12 and the fifth MOS switch 13 to be turned on, and the second MOS switch 10 and the third MOS switch 11 to be turned off. At this time, the external energy storage power supply 2, the first battery 3 and the second battery 4 are connected in parallel to supply power to the main device 5.

In the embodiment of the present invention, for example, the first preset condition, the second preset condition, the third preset condition, the fourth preset condition, the fifth preset condition, the sixth preset condition, the seventh preset condition, and the eighth preset condition are respectively set as follows: the first preset condition is that the voltage of the external energy storage power supply is lower than 95% of the normal value of the external energy storage power supply voltage for 500 milliseconds continuously, the second preset condition is that the first charging power duty cycle of the first battery and the second battery is reduced to 0, the third preset condition is that the first power value of the first battery 3 and the second power value of the second battery 4 are both less than 2% of their respective corresponding self-power, the fourth preset condition is that one of the first power value of the first battery 3 and the second power value of the second battery 4 exceeds 8% of their respective corresponding third preset threshold self-power, the fifth preset condition is that the power value of the current power supply battery is less than 92% of the power value of the current charging battery, the sixth preset condition is that the power value of the current power supply battery is less than 99% of the power value of the current charging battery, the seventh preset condition is that the voltage of the external energy storage power supply is lower than 96% of the normal value of the external energy storage power supply voltage for 200 milliseconds continuously, and the eighth preset condition is that the second charging power duty cycle of the charging battery is reduced to 0.

In the embodiment of the present invention, for example, the first preset condition, the second preset condition, the third preset condition, the fourth preset condition, the fifth preset condition, the sixth preset condition, the seventh preset condition, and the eighth preset condition are respectively set as follows: the first preset condition is that the voltage of the external energy storage power supply is lower than 90% of the normal value of the external energy storage power supply voltage for 1000 milliseconds continuously, the second preset condition is that the first charging power duty cycle of the first battery and the second battery is reduced to 0, the third preset condition is that the first power value of the first battery 3 and the second power value of the second battery 4 are both less than 5% of their respective corresponding self-power, the fourth preset condition is that one of the first power value of the first battery 3 and the second power value of the second battery 4 exceeds 3% of their respective corresponding third preset threshold self-power, the fifth preset condition is that the power value of the current power supply battery is less than 95% of the power value of the current charging battery, the sixth preset condition is that the power value of the current power supply battery is less than 99.5% of the power value of the current charging battery, the seventh preset condition is that the voltage of the external energy storage power supply is lower than 98% of the normal value of the external energy storage power supply voltage for 100 milliseconds continuously, and the eighth preset condition is that the second charging power duty cycle of the charging battery is reduced to 0.

In the embodiment of the present invention, for example, the first preset condition, the second preset condition, the third preset condition, the fourth preset condition, the fifth preset condition, the sixth preset condition, the seventh preset condition, and the eighth preset condition are respectively set as follows: the first preset condition is that the voltage of the external energy storage power supply is lower than 92% of the normal value of the external energy storage power supply voltage for 800 milliseconds continuously, the second preset condition is that the first charging power duty cycle of the first battery and the second battery is reduced to 0, the third preset condition is that the first power value of the first battery 3 and the second power value of the second battery 4 are both less than 4% of their respective corresponding self-power, the fourth preset condition is that one of the first power value of the first battery 3 and the second power value of the second battery 4 exceeds 5% of their respective corresponding third preset threshold self-power, the fifth preset condition is that the power value of the current power supply battery is less than 97% of the power value of the current charging battery, the sixth preset condition is that the power value of the current power supply battery is less than 99.7% of the power value of the current charging battery, the seventh preset condition is that the voltage of the external energy storage power supply is lower than 97% of the normal value of the external energy storage power supply voltage for 150 milliseconds continuously, and the eighth preset condition is that the second charging power duty cycle of the charging battery is reduced to 0.

In addition, an embodiment of the present invention also provides a power management device for a life support device, the device comprising: a processor and a memory; the memory is used to store one or more program instructions; the processor is used to run one or more program instructions to execute the steps of a power management method for a life support device as described in any of the above items.

In addition, an embodiment of the present invention further provides a computer-readable storage medium, on which a computer program is stored. When the computer program is executed by a processor, the steps of a power management method for a life support device as described in any one of the above items are implemented.

In the embodiment of the present invention, the processor may be an integrated circuit chip having the ability to process signals. The processor may be a general-purpose processor, a digital signal processor (DSP), an application specific integrated circuit (ASIC), a field programmable gate array (FPGA), a Programmable Gate Array (PGA) or other programmable logic devices, discrete gate or transistor logic devices, or discrete hardware components.

The methods, steps and logic block diagrams disclosed can be implemented or executed. The general processor can be a microprocessor or the processor can also be any conventional processor, etc. The steps of the method disclosed in the embodiments of the present invention can be directly embodied as a hardware decoding processor for execution, or can be executed by a combination of hardware and software modules in the decoding processor. The software module can be located in a mature storage medium in the field such as a random access memory, a flash memory, a read-only memory, a programmable read-only memory or an electrically erasable programmable memory, a register, etc. The processor reads the information in the storage medium and completes the steps of the above method in combination with its hardware.

The storage medium may be a memory, which may be, for example, a volatile memory or a nonvolatile memory, or may include both volatile and nonvolatile memory.

Among them, the non-volatile memory can be a read-only memory (ROM), a programmable ROM (PROM), an erasable programmable read-only memory (EPROM), an electrically erasable programmable read-only memory (EEPROM), or a flash memory.

The volatile memory may be a random access memory (RAM) which is used as an external cache. By way of example and not limitation, many forms of RAM are available, such as static RAM (SRAM), dynamic RAM (DRAM), synchronous DRAM (SDRAM), double data rate synchronous dynamic random access memory (DDRSDRAM), enhanced synchronous dynamic random access memory (ESDRAM), Synchlink DRAM (SLDRAM), and direct RAM bus random access memory (DRRAM).

The storage media described are intended to include, but are not limited to, these and any other suitable types of memory.

Those skilled in the art will appreciate that in one or more of the above examples, the functions described may be implemented using a combination of hardware and software. When software is used, the corresponding functions may be stored in a computer-readable medium or transmitted as one or more instructions or codes on a computer-readable medium. Computer-readable media include computer storage media and communication media, wherein communication media include any media that facilitates the transmission of computer programs from one place to another. Storage media may be any available media that can be accessed by a general or special purpose computer.

Although the present invention has been described in detail above by general description and specific embodiments, it is obvious to those skilled in the art that some modifications or improvements can be made on the basis of the present invention. Therefore, these modifications or improvements made on the basis of not departing from the spirit of the present invention all belong to the scope of protection claimed by the present invention.

We claim:

1. A power management method for a life support device, characterized in that the method is applied to a power management module, the method comprising:

performing a first real-time monitoring of a voltage of an external energy storage power supply;

controlling the external energy storage power supply to directly power a main device, charging a first battery and a second battery at the same time, and continuously monitoring the voltage of the external energy storage power supply in a first real-time manner in response to the voltage of the external energy storage power supply not meeting a first preset condition;

reducing a first charging power duty cycle of the first battery and the second battery according to a first preset ratio in response to the voltage of the external energy storage power supply meeting the first preset condition;

recording a number of first-stage adjustments and a corresponding first-stage adjustment time;

using the first preset number of recorded first-stage adjustment times and the corresponding first-stage adjustment times, predict the next first-stage voltage adjustment time;

calculating in sequence a first-stage adjustment time difference between two adjacent first-stage adjustment times;

determining whether the first-stage adjustment time difference of each first-stage adjustment satisfies a requirement of increasing or decreasing in sequence;

fitting a straight line adjustment function between the time differences of the first-stage adjustment and a corresponding number of first-stage adjustment times; and before a predicted next first-stage adjustment time, advancing a first preset time threshold, and continuing to reduce the first charging power duty cycle of the first battery and the second battery according to the first preset ratio;

wherein the first preset condition is set as the voltage of the external energy storage power supply is lower than a first preset threshold value for a continuous first time period, the first time period is 500 milliseconds to 1000 milliseconds, and the first preset threshold value is 90% to 95% of the normal value of the external energy storage power supply voltage.

2. A power management method for life support equipment as claimed in claim 1, characterized in that the method uses the first preset number of first-stage adjustment times and the corresponding first-stage adjustment times recorded to predict the next first-stage adjustment time, the method further comprising:

determining whether the current first-stage adjustment times reaches the first preset number;

continuing to perform the first real-time monitoring of the external energy storage power supply voltage in response to the current first-stage adjustment times not reaching the first preset number;

calculating a first average value of the time differences of the first-stage adjustment in response to the time differences of the first-stage adjustment not satisfying the requirement of increasing or decreasing in sequence; and using the first-stage adjustment function and/or the first average value to predict a next first-stage adjustment time.

3. A power management method for life support equipment according to claim 2, characterized in that the method further comprises:

performing a second real-time monitoring on the first charging power duty cycle of the first battery and the second battery;

continuing to perform second real-time monitoring on the first charging power duty ratio of the first battery and the second battery; the second preset condition is set as the first charging power duty ratio of the first battery and the second battery is reduced to 0 in response to the first charging power duty ratio of the first battery and the second battery not meeting the second preset condition;

performing a third real-time monitoring on the power levels of the first battery and the second battery in response to first charging power duty ratios of the first battery and the second battery meeting the second preset condition;

controlling the external power supply and the first battery and the second battery to be connected in parallel to supply power to the main device in response to the power levels of the first battery and the second battery meeting a third preset condition;

selecting and marking the battery with higher power level as the power supply battery, and marking the other battery as the rechargeable battery in response to the power levels of the first battery and the second battery not meeting the third preset condition; and switching the power supply battery to power the main device, and controlling the external power supply to only charge the rechargeable battery;

such that the first power value of the first battery and the second power value of the second battery do not reach their respective corresponding second preset thresholds, and the second preset thresholds corresponding to the first battery and the second battery are 1%-5% respectively.

4. A power management method for life support equipment as claimed in claim 3, characterized in that the method further comprises:

performing a fourth real-time monitoring on the power levels of the first battery and the second battery in response to the power levels of the first battery and the second battery not meeting the third preset condition;

performing a fifth real-time monitoring on the power levels of the current power supply battery and the current charging battery in response to the power levels of the first battery and the second battery meet a fourth preset condition;

continuing to perform fourth real-time monitoring on the power levels of the first battery and the second battery in response to the power levels of the current power supply battery and the current charging battery not meeting the fifth preset condition;

reselecting the battery with higher power level as the power supply battery and mark the other battery as the rechargeable battery in response to the power levels of the current power supply battery and the current rechargeable battery meeting the fifth preset condition; and switching the updated power supply battery to power the main device, controlling the external power supply to charge only the updated rechargeable battery, and continuing to perform a fourth real-time monitoring of the power of the first battery and the second battery;

wherein, the fourth preset condition is set as one of the first power value of the first battery and the second power value of the second battery exceeds their respective corresponding third preset thresholds, and the third preset thresholds corresponding to the first battery and the second battery are 3% to 8% respectively; the fifth preset condition is set as the power value of the current power supply battery is less than a first preset ratio of the power value of the current charging battery, and the first preset ratio is greater than or equal to 92% and less than or equal to 97%.

5. A power management method for life support equipment as claimed in claim 4, characterized in that the method further comprises:

performing a sixth real-time monitoring on the power levels of the current power supply battery and the current charging battery in response to the power levels of the first battery and the second battery not meeting the fourth preset condition;

continuing to perform fourth real-time monitoring on the power levels of the first battery and the second battery in response to the power levels of the current power supply battery and the current charging battery not meeting the sixth preset condition;

reselecting the battery with higher power level as the power supply battery and mark the other battery as the rechargeable battery in response to the power levels of the current power supply battery and the current rechargeable battery meeting the sixth preset condition;

switching the updated power supply battery to power the main device, controlling the external power supply to charge only the updated rechargeable battery, and continuing to perform a fourth real-time monitoring of the power of the first battery and the second battery; and setting the sixth preset condition as a second preset ratio that the power value of the current power supply battery is less than the power value of the current charging battery, and the second preset ratio is 99% to 99.7%.

6. A power management method for life support equipment as claimed in claim 5, characterized in that the method further comprises:

performing a seventh real-time monitoring on the voltage of the external energy storage power supply in response to the power levels of the first battery and the second battery not meeting the fourth preset condition;

continuing the seventh real-time monitoring of the voltage of the external energy storage power supply; setting the seventh preset condition as the voltage of the external energy storage power supply is lower than the fourth preset threshold value for a second consecutive time period, the second time period is 100 milliseconds to 200 milliseconds, and the fourth preset threshold value is 96% to 98% of the normal value of the voltage of the external energy storage power supply in response to the voltage of the external energy storage power supply not meeting the seventh preset condition;

reducing the second charging power duty cycle of the rechargeable battery according to a second preset ratio in response to the voltage of the external energy storage power supply meeting the seventh preset condition;

recording the number of second-stage adjustments and the corresponding second-stage adjustment time;

using the recorded second preset number of second-stage adjustment times and the corresponding second-stage adjustment times, predicting the next second-stage adjustment time;

advancing the second preset time threshold, and continuing to reduce the second charging power duty cycle of the rechargeable battery according to the second preset ratio before the predicted next second-stage adjustment time;

performing an eighth real-time monitoring on the second charging power duty cycle of the rechargeable battery;

continuing to perform the eighth real-time monitoring on the second charging power duty cycle of the rechargeable battery; and setting the eighth preset condition as the second charging power duty cycle of the rechargeable battery being reduced to 0 in response to the second charging power duty cycle of the rechargeable battery does not meet the eighth preset condition; and controlling the external power supply and the first battery and the second battery to be connected in parallel to supply power to the main device in response to the second charging power duty cycle of the rechargeable battery meeting the eighth preset condition.

7. A power management method for life support equipment as claimed in claim 6, characterized in that the method uses the second preset number of second-stage adjustment times and the corresponding second-stage adjustment times recorded to predict the next second-stage adjustment time, the method further comprising:

determining whether the current second-stage adjustment times reaches the second preset number;

continuing to perform a seventh real-time monitoring of the external energy storage power supply voltage in response to the current second-stage adjustment times not reaching the second preset number;

calculating in sequence the second-stage adjustment time difference between two adjacent second-stage adjustment times in response to the current second-stage adjustment times reaches the second preset number;

determining whether the time differences of each second-stage adjustment satisfy the requirement of increasing or decreasing in sequence;

fitting a linear adjustment function between each second-stage adjustment time difference and the corresponding second-stage adjustment times;

calculating a second average value of the time differences of the second-stage adjustment in response to the time differences of the second-stage adjustment do not satisfy the requirement of increasing or decreasing in sequence; and predicting the next second-stage adjustment time using the second-stage adjustment function and/or the second average value.

8. A power management system for life support equipment, characterized in that the system is applied to a power management module, and the system comprises: an external energy storage power supply voltage monitoring unit, a battery monitoring unit and a circuit control unit, the method further comprising:

performing a first real-time monitoring on the external energy storage power supply voltage by the external energy storage power supply voltage monitoring unit;

controlling, by the circuit control unit, the external energy storage power supply to directly power a main device, and charging a first battery and a second battery at the same time, and continuing, by the external energy storage power supply voltage monitoring unit, to perform first real-time monitoring on the voltage of the external energy storage power supply in response to the voltage of the external energy storage power supply not meeting a first preset condition;

reducing, by the circuit control unit, the first charging power duty cycle of the first battery and the second battery according to a first preset ratio in response to the voltage of the external energy storage power supply meeting the first preset condition; and recording, by the circuit control unit, a number of first-stage adjustment times and the corresponding first-stage adjustment time;

calculating, by the circuit control unit, in sequence a first-stage adjustment time difference between two adjacent first-stage adjustment times;

determining, by the circuit control unit, whether the first-stage adjustment time difference of each first-stage adjustment satisfies a requirement of increasing or decreasing in sequence;

fitting, by the circuit control unit, a straight line adjustment function between the time differences of the first-stage adjustment and a corresponding number of first-stage adjustment times; and continuing to reduce a first charging power duty ratio of the first battery and the second battery according to the first preset ratio by a first preset time threshold before the predicted next first-stage adjustment time;

wherein the first preset condition is set as the voltage of the external energy storage power supply being lower than a first preset threshold value for a continuous first time period, the first time period is 500 milliseconds-1000 milliseconds, and the first preset threshold value is 90% to 95% of the normal value of the external energy storage power supply voltage.

9. A power management device for a life support device, characterized in that the device comprises:

a memory that stores one or more program instructions; and a processor connected to the memory, the processor being configured to run one or more program instructions to execute the steps of a power management method for a life support device as claimed in claim 1.

10. A computer-readable storage medium, characterized in that a computer program is stored on the computer-readable storage medium, and when the computer program is executed by a processor, the steps of the power management method of a life support device as claimed claim 1 are implemented.

11. The power management method of claim 1, wherein the external energy storage power supply is a direct current (DC) power supply.

12. The power management system of claim 8, wherein the external energy storage power supply is a direct current (DC) power supply.

* * * * *